(12) United States Patent
Takai et al.

(10) Patent No.: US 6,468,626 B1
(45) Date of Patent: Oct. 22, 2002

(54) FLEXIBLE SHEET USED IN DISPOSABLE GARMENT

(75) Inventors: Hisashi Takai; Miou Suzuki, both of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 107 days.

(21) Appl. No.: 09/602,734

(22) Filed: Jun. 26, 2000

(30) Foreign Application Priority Data

Jun. 24, 1999 (JP) .......................................... 11-178882

(51) Int. Cl.[7] ............................. A61F 13/15; A61F 13/46
(52) U.S. Cl. ..................... 428/136; 428/131; 428/134; 428/137; 428/138; 604/365; 604/378; 604/383; 604/385.01; 604/385.101
(58) Field of Search ................................. 428/131, 132, 428/136, 137, 138; 604/365, 366, 370, 371, 374, 378, 383, 385.01, 385.101

(56) References Cited

U.S. PATENT DOCUMENTS

| | | | |
|---|---|---|---|
| 4,629,643 A | | 12/1986 | Curro et al. |
| 4,637,819 A | * | 1/1987 | Ouellette et al. ............ 428/131 |
| 4,741,941 A | * | 5/1988 | Englebert et al. ........... 15/209.1 |
| 5,536,555 A | | 7/1996 | Zelazoski et al. |
| 5,891,119 A | * | 4/1999 | Ta et al. ...................... 604/365 |
| 6,117,524 A | * | 9/2000 | Hisanaka et al. ............ 428/131 |

FOREIGN PATENT DOCUMENTS

| | | |
|---|---|---|
| EP | 0919212 A2 | 6/1999 |
| JP | 62-57551 | 3/1987 |

* cited by examiner

Primary Examiner—Harold Pyon
Assistant Examiner—Alicia Chevalier
(74) Attorney, Agent, or Firm—Baker & Daniels

(57) ABSTRACT

A flexible sheet 1 includes a plastic sheet and a fibrous assembly bonded to the lower surface of the sheet. The sheet is formed with projections, ribbon-shaped regions, fine slits defined between each pair of adjacent ribbon-shaped regions, bridge-like regions connecting each pair of adjacent ribbon-shaped regions and rising regions extending upward from edges of the ribbon-shaped regions. The fibrous assembly are partially exposed within the respective fine slits.

9 Claims, 7 Drawing Sheets

FLEXIBLE SHEET USED IN DISPOSABLE GARMENT

BACKGROUND OF THE INVENTION

This invention relates to a flexible sheet suitable to be used as a component of disposable body fluid-absorbent garments such as disposable diapers, urine absorbent pads or sanitary napkins, or of other garments such as disposable gowns conveniently used in medical fields.

FIG. 8 of the accompanying drawings is a perspective view showing a microapertured plastic sheet 110 described in Japanese Patent Application Disclosure No. 1987-57551 and claimed to afford a soft touch. The plastic sheet 110 is suitable for use as a topsheet and/or a backsheet of disposable diapers and formed on its upper surface with a plurality of cylindrical projections 120 which are, in turn, formed on their tops with microapertures 125. Such a plastic sheet 110 is described to offer a soft cloth-like touch.

In the case of the known plastic sheet, the microapertures formed on the tops of the respective cylindrical projections have their peripheral edges finely divided to present a petal-like appearance. When the plastic sheet is used, for example, as the topsheet of sanitary napkin, the petal-like peripheral edges will give the napkin wearer a soft touch as the petal-like peripheral edges rub her skin. However, an amount of menstrual discharge reaching a space defined between each pair of adjacent cylindrical projections rising on the upper surface of the plastic sheet can not easily move into the respective microapertures and may stay in the space. In other words, it is difficult for menstrual discharge to permeate the topsheet into an absorbent core as rapidly as possible.

SUMMARY OF THE INVENTION

It is an object of this invention to provide a flexible sheet that has a soft touch and at the same time to improve a permeability for body fluids than can be adapted for use as a component of body fluid-absorbent garment such as a disposable diaper or of other garments such as a disposable gowns conveniently used in medical fields.

According to this invention, there is provided a flexible sheet having upper and lower surfaces and being suitable for use as a component of disposable body fluid-absorbent garment, comprising:

the flexible sheet comprising a plastic sheet forming a part of the upper surface and a fibrous assembly bonded to a lower surface of the plastic sheet to form the remaining part of the upper surface of said flexible sheet and the entire lower surface of said flexible sheet;

the plastic sheet being formed with a plurality of projections occupying about 5~70% of a surface area of said plastic sheet each being convex upward with a height of about 0.01~0.5 mm from the upper surface and having a planar configuration circumscribed around a circle having a diameter of 0.25~5 mm, a plurality of ribbon-shaped regions extending in one direction in parallel one to another each having a thickness of about 0.001~0.05 mm and a width of about 0.03 ~1 mm, a plurality of fine slits extending in the one direction each being defined between each pair of adjacent ribbon-shaped regions, a plurality of bridge-like regions each extending from a pair of edges of adjacent ribbon-shaped regions transversely opposite to each other with the fine slit therebetween edges to connect the adjacent ribbon-shaped regions and a plurality of rising regions extending upward from the upper surface of the plastic sheet and undulating in the one direction so as to form sawtooth waves;

and the fibrous assembly comprising component fibers assembled by mechanically intertwining, heat-sealing adhesively bonding them together and containing at least one of thermoplastic synthetic fiber, chemical fiber and natural fiber wherein the component fibers are partially exposed within the respective fine slits of the plastic sheet.

DETAILED DESCRIPTION OF THE PREFERRED EMBODIMENTS

A flexible sheet proposed by this invention as one of the stock materials for making a disposable garment will be described in more details with reference to the accompanying drawings.

Figure 1:
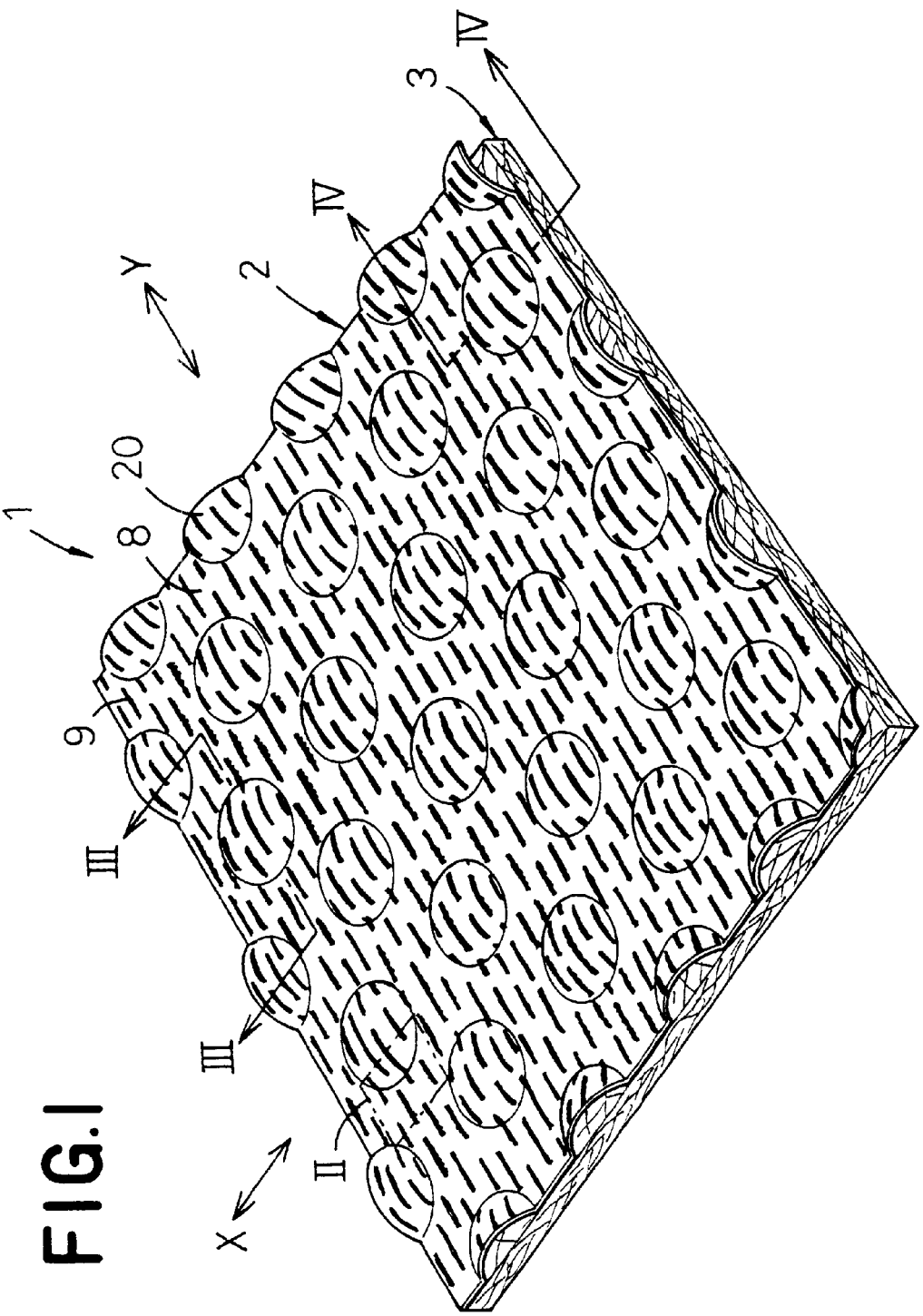
FIG. 1 is a perspective view showing a flexible sheet according to one embodiment of this invention.

A flexible sheet 1 shown by FIG. 1 in a perspective view comprises a plastic sheet 2 and a fibrous assembly 3 joined to the lower surface of the plastic sheet 2 so that the flexible sheet 1 has its upper surface defined by the plastic sheet 1 combined with the fibrous assembly 3 and its lower surface defined by the fibrous assembly 3 alone.

The plastic sheet 2 is of flexible nature and formed with a plurality of projections 20 which are convex upward from the upper surface of the plastic sheet 2, a plurality of ribbon-shaped regions 8 extending in parallel one to another in a direction indicated by a double-headed arrow Y and a plurality of fine slits 9 lying between each pair of the ribbon-shaped regions 8, 8 adjacent to each other in a direction indicated by a double-headed arrow X and extending in the direction Y.

Figure 2:
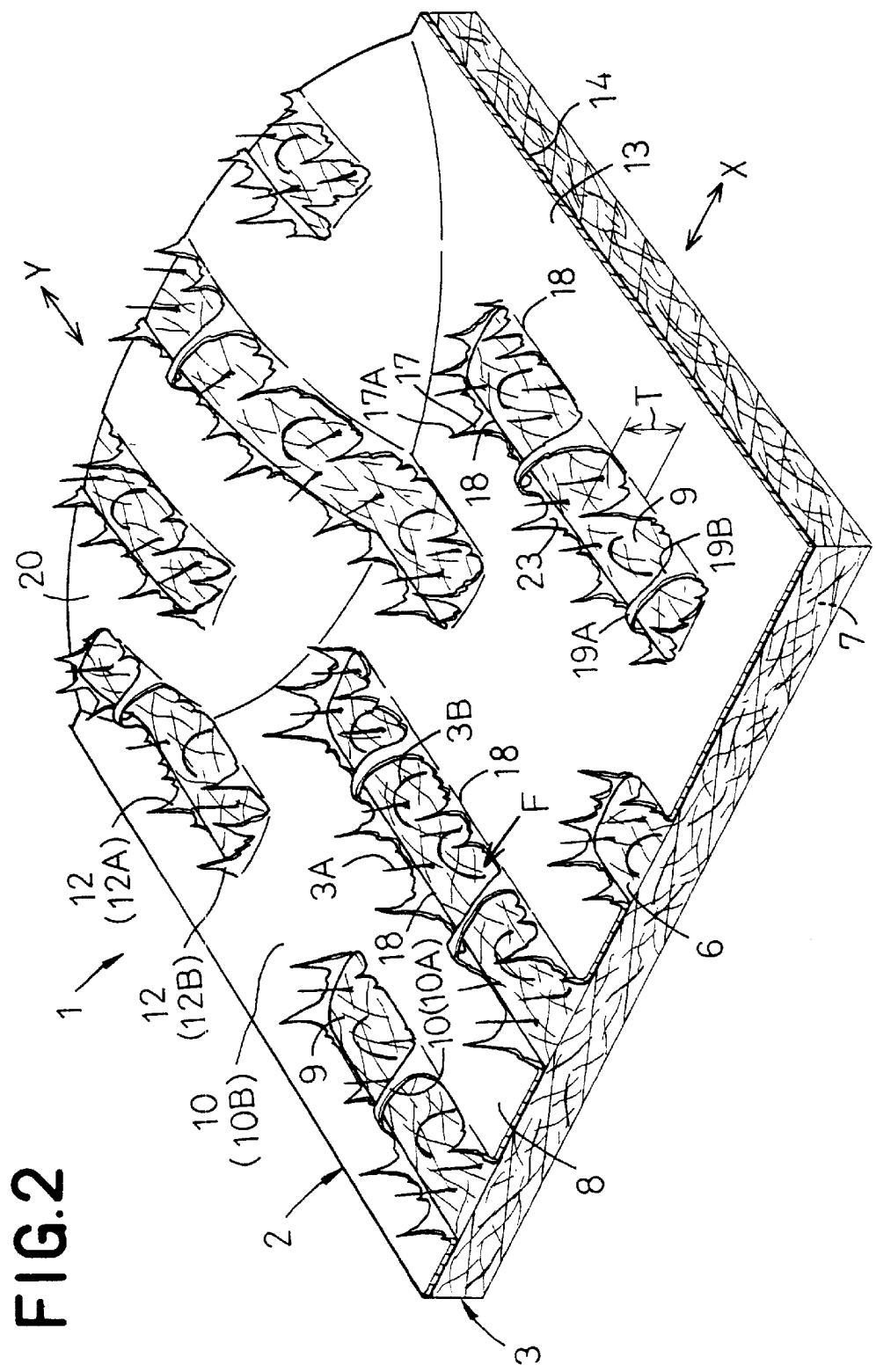
FIG. 2 is a fragmentary perspective view showing a part of FIG. 1 in an enlarged scale.

FIG. 2 is a scale-enlarged fragmentary perspective view showing a zone II enclosed by a broken line in FIG. 1. The zone II extends between a pair of the adjacent projections 20, 20 and the plastic sheet 2 is relatively flat in this zone II. The plastic sheet 2 is further formed along edges of the ribbon-shaped regions 8, 8 with a plurality of rising regions 12 extending upward from the upper surface 13 of the respective ribbon-shaped regions 8. Each pair of the adjacent ribbon-shaped regions 8, 8 have their respective one edges 18 directly opposed to each other and connected to each other by bridge-like regions 10 extending in the direction X across the fine slits or apertures 9 defined between the one edges of the adjacent ribbon-like regions 8, 8 directly opposed to each other. The rising regions 12 irregularly undulate in the direction Y so as to form sawtooth-like waves. The fibrous assembly 3 is covered with the ribbon-shaped regions 8 of the plastic sheet 2 and exposed in the respective fine slits 9 within which component fibers partially extend upward so as to describe straight lines or circular arcs.

Figure 3:
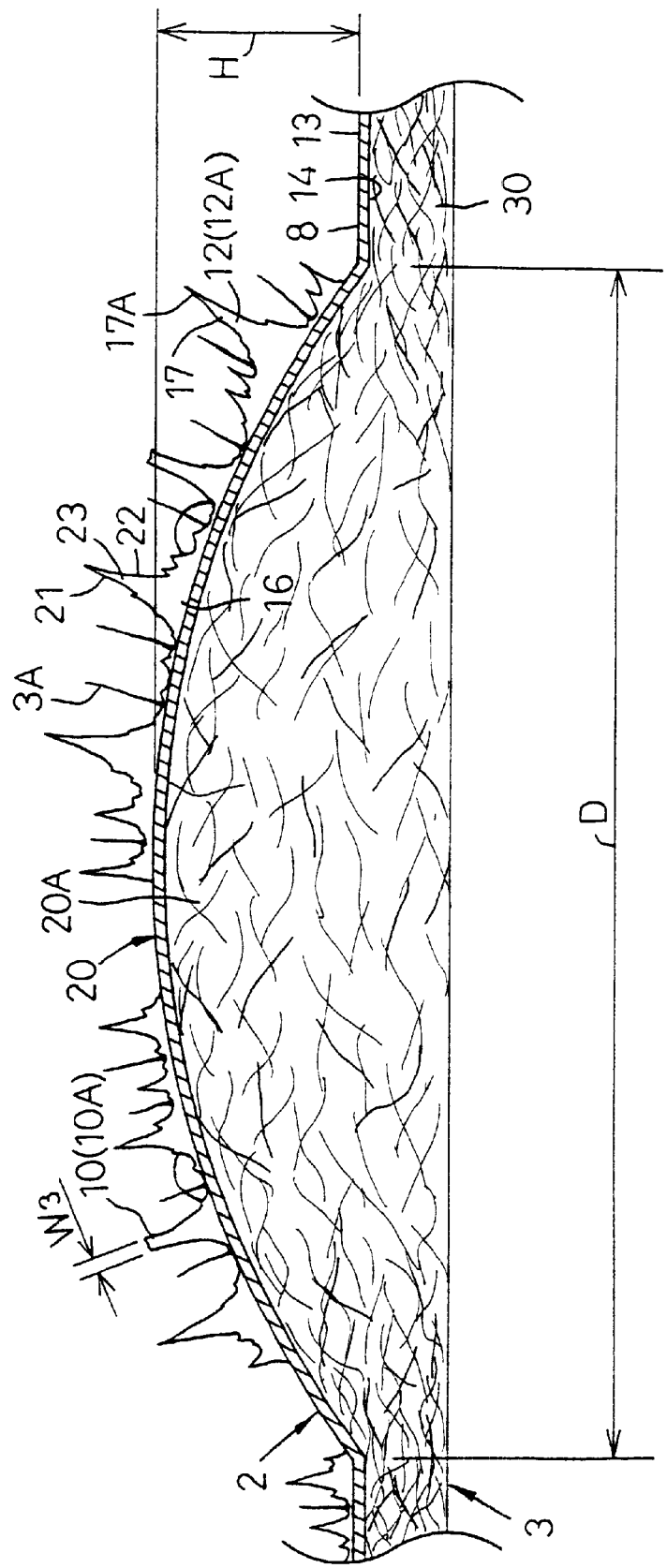
FIG. 3 is a sectional view taken along line III—III in FIG. 1.
Figure 4:
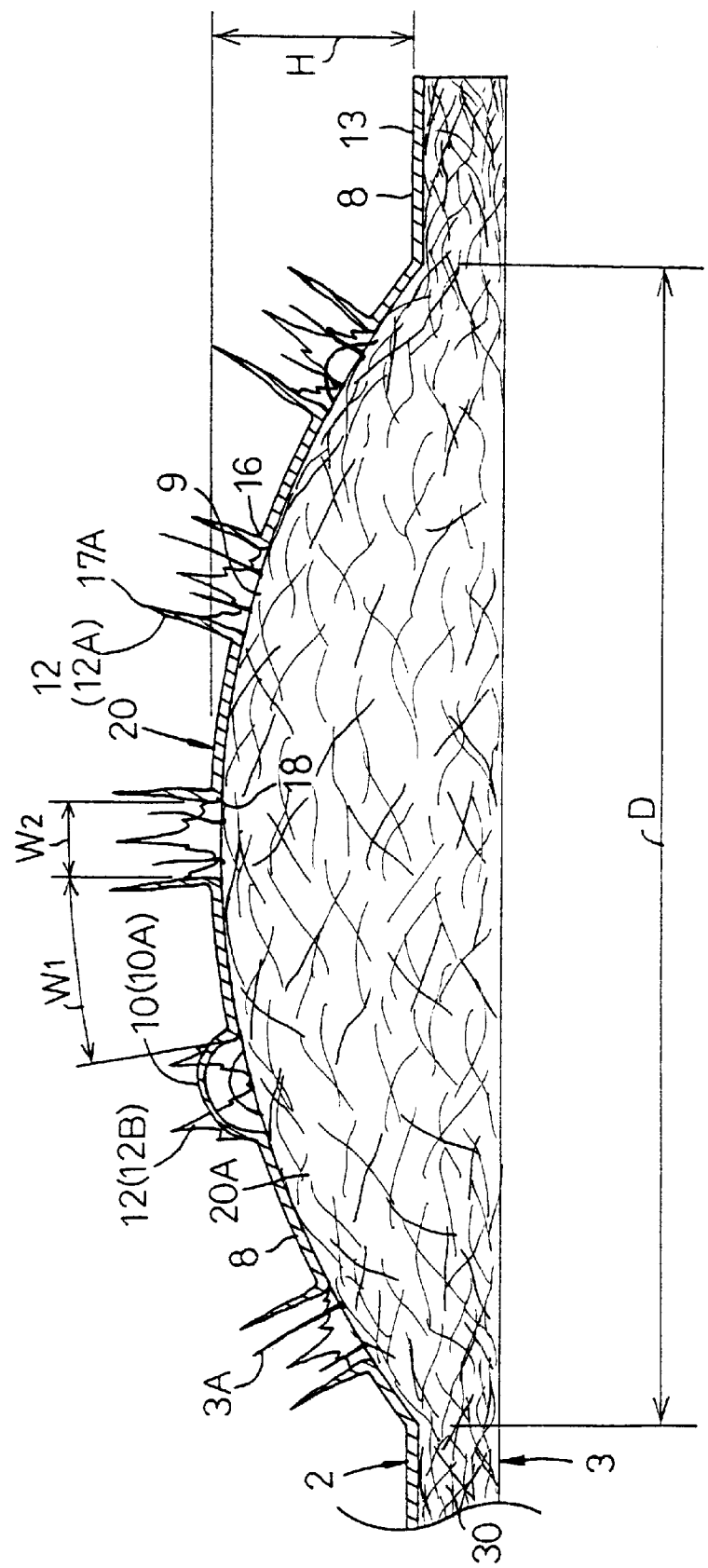
FIG. 4 is a sectional view taken along line IV—IV in FIG. 1.

FIGS. 3 and 4 are sectional views taken along lines III—III and IV—IV of FIG. 1, respectively, extending through the projection 20.

Referring to FIGS. 3 and 4, the ribbon-shaped regions 8 of the plastic sheet 2 have a thickness of about 0.001~0.05 mm and a width $W_1$ of about 0.03~1 mm as measured between each pair of the fine slits 9, 9 adjacent to each other in the direction X. Most of the fine slits 9 extend in the direction Y and preferably have their width $W_2$ of about 0.05~1 mm and their length corresponding to about 1.5 times of the width $W_2$ or larger. Each of the projections 20 has a height H of about 0.01~0.5 mm and a diameter D of about 0.25~5 mm. These projections 20 occupy about 5~70% of a surface area of the plastic sheet 2 inclusive of the ribbon-shaped regions 8 and the fine slits 9. The diameter D corresponds to the diameter of a circle circumscribed about a planar configuration of the projection 20. The planar configuration of the projection 20 and the distribution of these projections 20 over the plastic sheet 2 are not critical and a specific embodiment as illustrated may be adopted without departing from the scope of this invention, in which a plurality of projections 20 defined by uniform diameter D and uniform planar configuration are arranged at substantially regular intervals in the direction X as well as in the direction Y. Similar to FIG. 2, FIGS. 3 and 4 also illustrate that the regions of the plastic sheet 2 defining the projections 20 are also formed with the ribbon-shaped regions 8 and the fine slits 9.

The bridge-like zones 10 are arranged intermittently in the direction Y. The bridge-like regions 10 comprise those of one type 10A which are convex upward from the upper surfaces 13 of the adjacent ribbon-shaped regions 8, 8 so as to describe circular arcs and those of the other type 10B extending on the same level with the ribbon-shaped regions 8, 8. The bridge-like region 10A describing a circular arc may have its proximal ends 19A appearing as if these proximal ends 19A immediately extend from the ribbon-shaped zones 8 or may have its proximal ends 19B appearing as if the proximal ends 19B extend from the tops of the rising regions 12 (See FIG. 2). Preferably, the bridge-like region 10 has a width $W_3$ of at least about 0.001 ~2 mm as measured in the direction Y (See FIGS. 2 and 3). The bridge-like region 10 connects each pair of the adjacent ribbon-shaped regions 8, 8 with each other and thereby holds the ribbon-shaped regions 8 on the upper surface of the fibrous assembly 3 even if the ribbon-shaped regions 8 are partially peel off from the fibrous assembly 3. Of the bridge-like regions 10, the bridge-like regions 10A describing circular arcs contribute to improvement of a cushioning effect afforded by the flexible sheet 1.

Most of the rising regions 12 identified by reference numeral 12A are formed by portions of the plastic sheet 2 extending upward from the edges 18 of the ribbon-like regions 8 and each of the rising regions 12A comprises a proximal end 16 contiguous to the ribbon-shaped region 8 and a free end 17 extending upward from the proximal end 16. Upper edges 17A of the respective free ends 17 undulate along the respective edges 18. A height T of such upper edges 17A as measured from the upper surface 13 of the ribbon-shaped regions 8 varies in a range of about 0~1 mm.

It is meant by the upper edge 17A having a height T of 0 mm that the transverse extent of the ribbon-shaped regions 8 terminates at its opposite edges 18 and these edges 18 have none of the rising regions 12. Some of the rising regions 12 identified by reference numeral 12B are formed along opposite edges of the bridge-shaped region 10 so as to undulate in the direction X and have the substantially the same as the rising regions 12A (See FIG. 2).

One embodiment in which the upper edges 17A of the rising regions 12A undulate so as to form sawtooth waves will be described in more details with reference to FIGS. 2 and 3. The rising regions 12A comprise irregularly repeating triangular or substantially triangular portions 23 each defined by a substantially rightward ascendant oblique side 21, a substantially leftward ascendant oblique side 22 and the proximal end 16 extending between these two oblique sides 21, 22. The rising regions 12B also undulate in the similar manner to the rising regions 12A. The rising regions 12 comprising the rising regions 12A, 12B have a thickness equal to or less than the thickness of the ribbon-shaped regions 8 so that the rising regions 12 may be smoothly deformed as they come in contact with a wearer's skin and consequently the flexible sheet 1 may give its surface a smooth and soft velvet touch.

While it will be difficult to visually recognize the individual rising regions 12, a plurality of rising regions 12 as a whole give the upper surface of the flexible sheet 1 a fluffy appearance. The rising regions 12 diffusively reflect the light incident thereupon and thereby alleviate surface gloss which otherwise might be presented by the upper surface 13 of the plastic sheet 2.

The plastic sheet 2 is configured so that the projections 20 may have hollow interior spaces 20A to be filled with the component fibers of the fibrous assembly 3. The fibrous assembly 3 as a whole may have a substantially uniform fiber density or may have a lower fiber density in the hollow interior spaces 20A of the respective projections 20 than regions 30 surrounding these projections 20. The term "fiber density" used herein means the number of the component fibers per unit volume. A higher fiber density generally results in the correspondingly higher weight density per unit volume.

The plastic sheet 2 preferably has a breathability of about 5~700 $cm^3/cm^2 \cdot sec$ as measured according to the prescription of JIS(Japanese Industrial Standards)-L-1096 and a moisture resistance of about 0~200 mm as measured according to the prescription of JIS-L-1092. The plastic sheet 2 is made of material selected from a group including a hydrophobic or hydrophilic thermoplastic sheet and a hydrophobic thermoplastic sheet subjected to a treatment making it hydrophilic.

The fibrous assembly 3 is made of material selected from a group including thermoplastic synthetic fiber, chemical fiber such as rayon fiber, a mixture of these synthetic fiber and chemical fiber, and such synthetic fiber and/or chemical fiber mixed with cotton fiber and/or pulp fiber. The fibrous assembly 3 contains hydrophilic fiber of about 5 w/w % or higher, preferably of about 10 w/w % or higher, more preferably of about 20 w/w % or higher. Preferably, the assembly 3 is of flexible nature and has a basis weight of about 2~50 $g/m^2$. More preferably, the component fibers are mechanically intertwined and heat-sealed or adhesively bonded together to form nonwoven fabric. For example, the nonwoven fabric is preferably used, which contains thermoplastic synthetic fiber or chemical fiber having a fineness of about 0.05~15 deniers. The nonwoven fabric containing thermoplastic synthetic fiber may be selected from a group including a spun bond nonwoven fabric, a point bond nonwoven fabric, a thermal bond nonwoven fabric such as an air-through nonwoven fabric, a melt blown nonwoven fabric and a spun lace nonwoven fabric. In its thickness direction, the fibrous assembly 3 preferably has a breathability of about 5~700 cm$^3$/cm$^2$ · sec as measured according to the prescription JIS-L-1096 and a moisture resistance of about 0~200 mm as measured according to the prescription of JIS-L-1092. Joining the assembly 3 to the plastic sheet 2 may be carried out using heat- or supersonic-sealing or a suitable adhesive agent such as a hot melt adhesive agent.

As will be apparent from FIGS. 2~4, the component fiber 3A of the fibrous assembly 3 partially extend through the respective fine slits 9 upward beyond the level of the ribbon-shaped regions 8 of the plastic sheet 2 so as to described straight lines or circular arcs between the rising regions 12 undulating along each pair of the edges opposed to each other with the associated fine slits 9 therebetween. Most of the such component fibers 3A extend upward to the height of about 0.02~5 mm, preferably of about 0.05~1 mm from the upper surface 13 of the ribbon-shaped regions 8 and do not extend upward beyond the tops of the respective rising regions 12. While not as effective as the rising regions 12 of the plastic sheet 2, those of the component fibers 3A extending upward also serve to give the surface of the flexible sheet 1 a soft velvet touch and, in addition, to prevent the rising regions 12 from collapsing by contacting the rising regions 12 from below and thereby to maintain the fine slits 9 open. Unless none of the component fibers 3A extend upward beyond the tops of the rising regions 12, the component fibers 3A do not obstruct the rising regions 12 from presenting the soft velvet touch peculiar to the rising regions 12. The projections 20 serve, in cooperation with the rising regions 12 or independently thereof, to space the flexible sheet 1 from a wearer's skin and thereby to improve a breathability maintained between the sheet 1 and the skin. The projections 20 have their hollow interior spaces filled with the component fibers 3A of the fibrous assembly 3 and therefore do not easily collapse even they come in contact with a wearer's skin.

The flexible sheet 1 obtained in this manner can be used as the liquid-pervious topsheet in disposable body fluid-absorbent garment such as disposable diapers or sanitary napkins since the flexible sheet 1 can be obtained in the form of a sheet offering a soft velvet touch, a sheet affording a comfortable touch as well as a breathability or a sheet affording a breathability, a liquid-permeability and a comfortable touch. The flexible sheet 1 can be used also as the backsheet in the garment. Furthermore, the sheet 1 is suitable also as cloth for disposable garment such as disposable gowns conveniently used in medical fields, for example, during a surgical operation, or as wipes for glasses.

The comfortable touch of this flexible sheet 1 is achieved principally by a flexibility of the plastic sheet 2 itself and the rising regions 12 thereof, on one hand, and by a flexibility of the fibrous assembly 3 itself and the component fibers 3A thereof extending upward, on the other hand. The breathability of the flexible sheet 1 is ensured in the thickness direction of the sheet 1 by the fine slits 9 of the plastic sheet 2 and the interstices among the component fibers of the fibrous assembly 3, on one hand, and through a gap between the plastic sheet 2 and a wearer's skin by the rising regions 12 as well as the projections 20 of the plastic sheet 2. The liquid-permeability of the flexible sheet 1 is ensured by the fine slits 9 and the interstices of the component fibers 3A and largely depends on whether the plastic sheet 2 and the fibrous assembly 3 are hydrophilic or not. For example, the hydrophilic rising regions 12 of the plastic sheet 2 will facilitate body fluids to be collected into the fine slits 9 and the amount of body fluids thus collected into the fine slits 9 will be facilitated to move downward under the effect of capillarity so far as the component fibers 3A of the fibrous assembly 3 are at least partially hydrophilic. Particularly when the component fibers 3A extending upward within the respective fine slits 9 are hydrophilic, the amount of body fluids will be facilitated to move downward from the respective fine slits 9 even if the rising regions 12 are not hydrophilic. With the fibrous assembly 3 being substantially hydrophilic but containing hydrophobic component fibers of about 3~30 w/w %, these hydrophobic component fibers may assist said amount of body fluids to move downward. It should be understood, however, that the plastic sheet 2 as well as the fibrous assembly 3 may be hydrophilic or hydrophobic if the particular application of the flexible sheet 1 does not require the liquid-permeability.

When the flexible sheet 1 is used as the liquid-pervious topsheet in body fluid-absorbent garment, an amount of body fluids discharged on the ribbon-shaped regions 8 of the garment, on one hand, flows on the ribbon-shaped regions 8, then through zones each defined between each pair of the adjacent rising regions 12, 12, e.g., zones in which the tops 17A of the respective rising regions 12 lie at the height T of 0 mm and in the vicinity of such zones into the fine slits 9 as indicated by an arrow F (See FIG. 2) and is finally absorbed by the absorbent core via the fibrous assembly 3 overlying the absorbent core. This means that a liquid-permeability of the flexible sheet 1 is not obstructed by the rising regions 12 even when these rising regions 12 lie along the edges of the fine slits 9. Another amount of body fluids discharged on the projections 20 of the garment, on the other hand, flows downward off from a wearer's skin. In this way, the flexible sheet 1 can be advantageously used to alleviate a feeling of uncomfortable wetness. Such effect can be further improved by distributing the component fibers of the fibrous assembly so that the fiber density is relatively low in the hollow interior spaces of the projections 20 and relatively high around these projections 20. This is because the amount of body fluids discharged on the projections 20 tends to move from the zone of the relatively low fiber density toward the zone of the relatively high fiber density.

Figure 5:
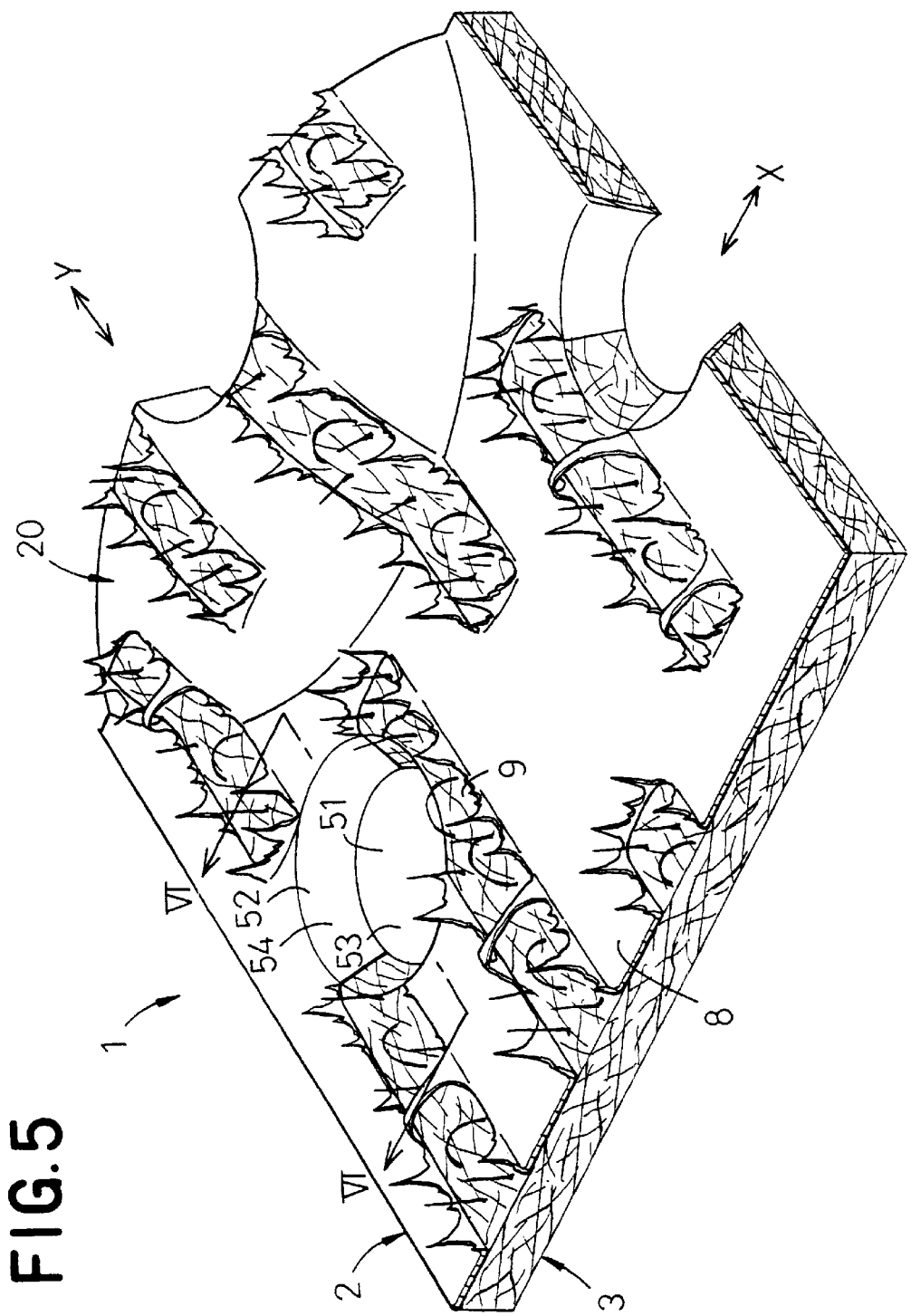
FIG. 5 is a view similar to FIG. 2 but showing an alternative embodiment of this invention.
Figure 6:
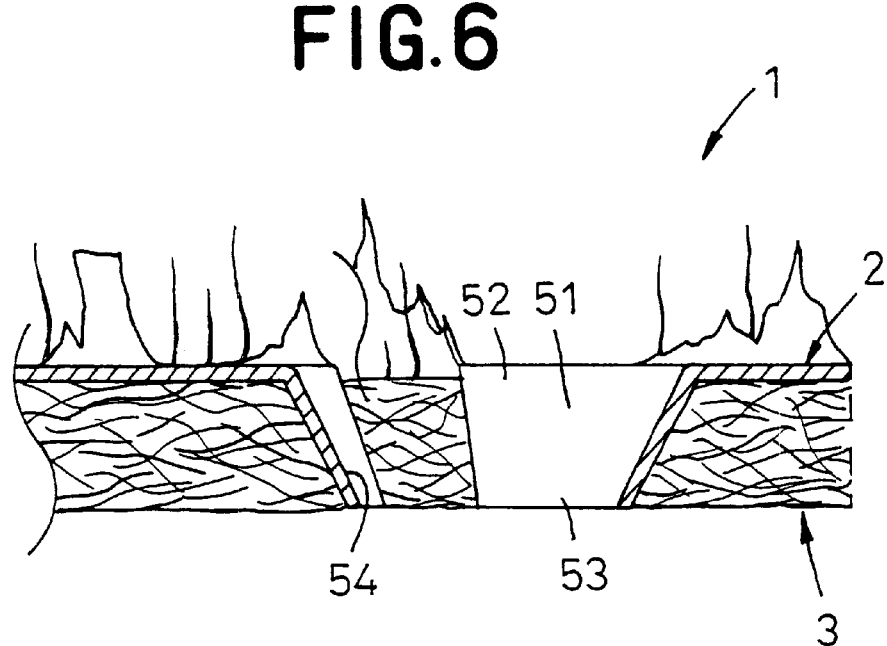
FIG. 6 is a sectional view taken along a line VI—VI in FIG. 5.

FIG. 5 is a view similar to FIG. 2 but showing an alternative embodiment of this invention and FIG. 6 is a sectional view taken along line VI—VI in FIG. 5. The flexible sheet 1 according to this embodiment is formed with a plurality of tubular regions 51 extending through the plastic sheet 1 from its upper surface to its lower surface. Each of the tubular regions 51 comprises an upper opening 52, a lower opening 53 and a tubular wall 54 extending between the two openings 52, 53. Each of the openings 52, 53 has a diameter of 0.1~5 mm, preferably of 1.5~5 mm and the upper openings 52 totally occupies 1~80%, preferably of 5~70% of the upper surface of the flexible sheet 1. The tubular wall 54 is preferably tapered from the upper opening 52 toward the lower opening 53. The tubular region 51 has a vertical dimension of about 0.1~5 mm, preferably of about 0.2~3 mm. When the flexible sheet 1 having said lower openings 53 not covered with the fibrous assembly 3 is used as the liquid-pervious topsheet of disposable diapers, the diapers are constructed so that the lower openings 53 overlie the upper surface of the absorbent core. It is also possible without departing from the scope of this invention to form the projections 20 of the plastic sheet 2 with said tubular regions 51.

Figure 7:
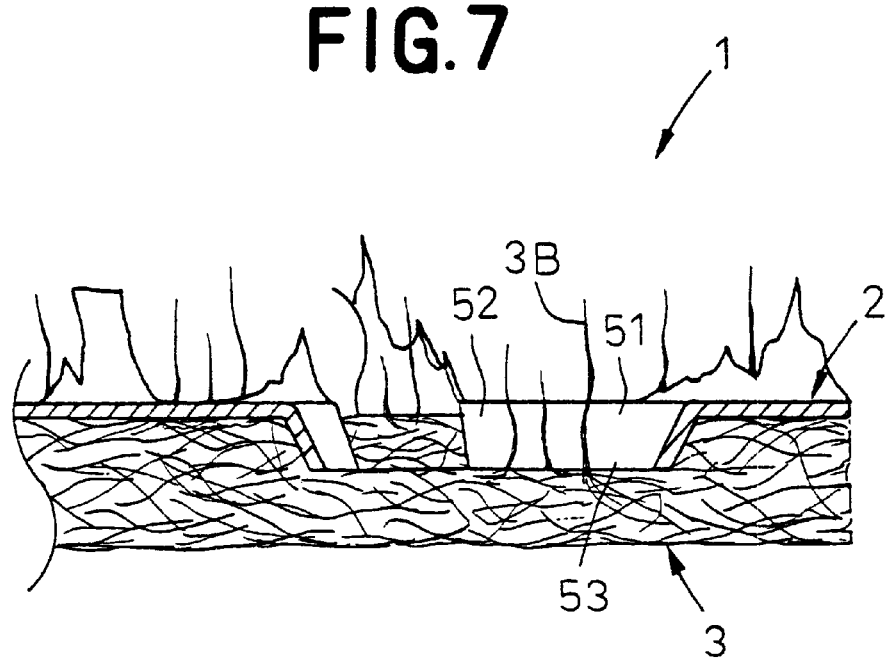
FIG. 7 is a view similar to FIG. 6 but showing another alternative embodiment of this invention.
Figure 8:
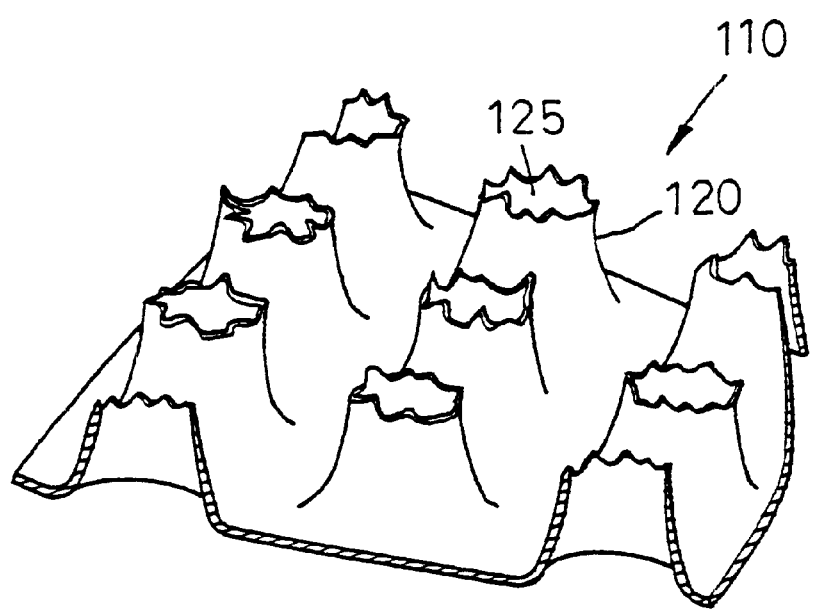
FIG. 8 is a perspective view exemplarily showing the plastic sheet of prior art.

FIG. 7 is a view similar to FIG. 5 but showing another alternative embodiment of this invention. In the case of the flexible sheet 1 according to this invention, the lower openings 53 of the respective tubular regions 51 are covered with the fibrous assembly 3 and the component fibers 3B exposed within the lower openings 53 partially extend upward. The component fibers 3B extend upward beyond the upper openings 52 and thereby serve to afford the flexible sheet 1 the same soft touch as afforded by the component fibers 3A. The component fibers 3B of hydrophilic nature will facilitate body fluids to be guided through the tubular regions 51 downward under the effect of capillarity. The tubular regions 51 of hydrophobic nature will further improve the liquid guiding effect ensured by the hydrophilic component fibers 3B. It is possible for the flexible sheet 1 according to this embodiment to form the projections 20 with the tubular regions 20.

The flexible sheet according to this invention comprises the plastic sheet by which the upper surface of the flexible sheet is partially formed and the fibrous assembly by which the lower surface of the flexible sheet is partially formed. The plastic sheet is formed with a plurality of projections which are convex upward from the upper surface thereof, a plurality of fine slits extending in one direction in parallel one to another and a plurality of rising regions undulating along edges of the plastic sheet defining the respective fine slits. This flexible sheet can be advantageously used for making a disposable garment. Specifically, the projections and the rising regions serve to prevent the flexible sheet and a wearer's skin from coming in close contact with each other and thereby maintains a desired breathability between them. The presence of the rising regions ensures that flexible sheet to offers a comfortable touch. The flexible sheet used as the topsheet of disposable diapers or sanitary napkins accelerates body fluids to move from zones each pair of adjacent rising regions to the absorbent core underlying the flexible sheet. The tubular regions extending through the flexible sheet from its upper surface to its lower surface further improve a liquid-permeability of body fluids.

With the flexible sheet having a plurality of tubular regions extending from its upper surface to its lower surface, the component fibers of the fibrous assembly extending upward from the lower openings of the tubular regions serve to improve the comfortable touch of the flexible sheet, on one hand, and to improve the liquid guiding effect of the tubular regions, on the other hand.

What is claimed is:

1. A flexible sheet for use as a component of a disposable garment comprising:
   a flexible plastic sheet having an upper surface, a lower surface, a thickness of from about 0.001 to about 0.05 mm, a plurality of substantially flat portions having widths of from about 0.03 to about 1 mm and extending in parallel to one another in a first direction, and a plurality of intermittent apertures extending in said first direction between said substantially flat portions so as to form a plurality of aperture rows extending in parallel one to another in said first direction,
   pairs of said flat portions having said aperture rows therebetween being interconnected by a plurality of bridge portions that extend therebetween and across said aperture rows, said bridge portions extending across the respective aperture rows are formed intermittently in a second direction orthogonal to the first direction,
   providing two types of bridge portions, those which extend upward or downward from the upper surfaces of the flat portions to the upper surfaces of the respectively adjacent flat portions so as to describe arcs and those which are flush with the flat portion,
   said intermittent apertures being defined by edges of said substantially flat portions which extend in said first direction and edges of said bridges portions which extend in said second direction,
   said substantially flat portions being formed at least along said edges thereof which extend in said first direction with a plurality of substantially tooth-shaped portions which extend upward from upper surfaces of said substantially flat portions,
   a plurality of circular projections extending convexly on the upper surface of the flexible plastic sheet and occupying from about 5 to about 70 percent of the total surface area of the flexible plastic sheet, said projections have heights of from about 0.01 to about 0.05 mm and diameters of from about 0.25 to about 5 mm, each of said plurality of circular projections containing a plurality of said intermittent apertures and bridge elements; and
   a fibrous layer joined to the lower surface of the flexible plastic sheet, said fibrous layer comprising component fibers that are assembled by mechanically intertwining and heat-sealing adhesively bonding them together, said fibrous layer further comprising at least one of thermoplastic synthetic fibers, chemical fibers and natural fibers and being partially exposed within the apertures of said flexible plastic sheet.

2. The flexible sheet according to claim 1, wherein a majority of said intermittent apertures have widths of about 0.05 to about 1 mm and lengths corresponding to at least about 1.5 times of the widths thereof.

3. The flexible sheet according to claim 1, wherein edges of said bridge portions are formed with a plurality of second rising regions undulating in a direction orthogonal to said one direction so as to define sawtooth portions.

4. The flexible sheet according to claim 1, wherein said fibrous layer comprises thermoplastic synthetic fibers or chemical fibers having a fineness of about 0.05 to about 15 deniers.

5. The flexible shoot according to claim 1, wherein said fibrous layer is selected from the group consisting of thermal bond nonwoven fabrics, melt blown nonwoven fabrics, spun lace nonwoven fabrics and mixtures thereof.

6. The flexible sheet according to claim 1, wherein said flexible plastic sheet is formed with a plurality of tubular passages each extending therethrough downward from said upper surface to said lower surface and having a diameter of about 0.15 mm at said upper surface.

7. The flexible sheet according to claim 6, wherein said component fibers partially extend upward within said tubular passages beyond upper ends of said tubular passages.

8. The flexible sheet according to claim 1, wherein said projections on said flexible plastic sheet have hollow interior spaces that are filled with said component fibers.

9. The flexible sheet according to claim 8, wherein said fibrous layer has a fiber density that is higher in said hollow spaces than in zones around said hollow spaces.

* * * * *